(12) United States Patent
Frantz et al.

(10) Patent No.: US 7,474,918 B2
(45) Date of Patent: Jan. 6, 2009

(54) THORACIC IMPEDANCE MONITOR AND ELECTRODE ARRAY AND METHOD OF USE

(75) Inventors: Ann K. Frantz, Las Vegas, NV (US); Philip Hamski, Henderson, NV (US)

(73) Assignee: Noninvasive Medical Technologies, Inc., Las Vegas, NV (US)

( * ) Notice: Subject to any disclaimer, the term of this patent is extended or adjusted under 35 U.S.C. 154(b) by 25 days.

(21) Appl. No.: 11/088,307

(22) Filed: Mar. 24, 2005

(65) Prior Publication Data

US 2005/0215918 A1  Sep. 29, 2005

Related U.S. Application Data

(60) Provisional application No. 60/556,394, filed on Mar. 24, 2004.

(51) Int. Cl.
*A61B 5/05* (2006.01)

(52) U.S. Cl. .................................................... 600/547

(58) Field of Classification Search ................ 600/547, 600/587, 536, 506, 437, 554
See application file for complete search history.

(56) References Cited

U.S. PATENT DOCUMENTS

| | | | |
|---|---|---|---|
| 3,149,627 A | | 9/1964 | Bagno |
| 3,212,496 A | * | 10/1965 | Preston ...................... 600/484 |
| 3,340,867 A | * | 9/1967 | Kubicek et al. ............. 600/526 |
| 3,452,743 A | | 7/1969 | Rieke |
| 3,570,474 A | | 3/1971 | Jonson |
| 3,608,543 A | * | 9/1971 | Longini et al. .............. 600/536 |
| 3,730,171 A | * | 5/1973 | Namon ....................... 600/526 |
| 3,742,936 A | | 7/1973 | Blanie et al. |
| 3,835,839 A | | 9/1974 | Brown |
| 3,835,840 A | | 9/1974 | Mount |
| 3,847,142 A | | 11/1974 | Williams, Jr. et al. |
| 3,871,359 A | | 3/1975 | Pacela |
| 3,874,368 A | | 4/1975 | Asrican |
| 3,882,851 A | | 5/1975 | Sigworth |
| 3,976,052 A | | 8/1976 | Junginger et al. |
| 3,994,284 A | | 11/1976 | Voelker |
| 3,996,925 A | | 12/1976 | Djordjevich |
| 4,137,910 A | | 2/1979 | Murphy |
| RE30,101 E | * | 9/1979 | Kubicek et al. ............. 600/526 |

(Continued)

FOREIGN PATENT DOCUMENTS

EP  1 224 908 A1  7/2002

*Primary Examiner*—Max Hindenburg
*Assistant Examiner*—Brian Szmal
(74) *Attorney, Agent, or Firm*—Panitch Schwarze Belisario & Nadel LLP

(57) ABSTRACT

A portable thoracic impedance monitor for monitoring thoracic fluid levels, an electrode array assembly having a single linear electrode array lead with first, second, third, and fourth electrodes arranged sequentially and axially along the linear electrode array lead, and a method of use of the thoracic impedance monitor. A measurement of the user's thoracic impedance is obtained by connecting the second electrode to the user's body at the junction of the clavicles, superior to the sternum, the third electrode to the user's body at the xiphoid-sternal junction, and the first and fourth electrodes to the user's body substantially along a centerline of the user's sternum respectively at a first pre-determined distance above the second electrode and a second predetermined distance below the third electrode, followed by initiating operation of the monitor.

27 Claims, 10 Drawing Sheets

U.S. PATENT DOCUMENTS

| | | | |
|---|---|---|---|
| 4,204,545 A | 5/1980 | Yamakoshi | |
| 4,205,688 A | 6/1980 | Hauser et al. | |
| 4,258,720 A | 3/1981 | Flowers | |
| 4,305,400 A | 12/1981 | Logan | |
| 4,328,814 A * | 5/1982 | Arkans | 600/393 |
| 4,361,049 A | 11/1982 | Volgyesi | |
| 4,422,458 A | 12/1983 | Kravath | |
| 4,432,374 A | 2/1984 | Osanai | |
| 4,437,469 A | 3/1984 | Djordjevich et al. | |
| 4,450,527 A * | 5/1984 | Sramek | 600/484 |
| 4,548,211 A | 10/1985 | Marks | |
| 4,562,843 A * | 1/1986 | Djordjevich et al. | 600/485 |
| 4,641,260 A | 2/1987 | Fukukita et al. | |
| 4,649,932 A | 3/1987 | Smith | |
| 4,676,253 A | 6/1987 | Newman et al. | |
| 4,733,670 A | 3/1988 | Hays et al. | |
| 4,757,824 A | 7/1988 | Chaumet | |
| 4,805,621 A | 2/1989 | Heinze et al. | |
| 4,807,638 A * | 2/1989 | Sramek | 600/485 |
| 4,823,797 A | 4/1989 | Heinze et al. | |
| 4,836,214 A * | 6/1989 | Sramek | 600/506 |
| 4,862,361 A | 8/1989 | Gordon et al. | |
| 4,870,578 A * | 9/1989 | Vysin et al. | 600/509 |
| 4,905,705 A | 3/1990 | Kizakevich et al. | |
| 4,919,145 A * | 4/1990 | Marriott | 600/536 |
| 4,955,383 A * | 9/1990 | Faupel | 600/407 |
| 4,979,110 A | 12/1990 | Albrecht et al. | |
| 5,025,784 A | 6/1991 | Shao et al. | |
| 5,046,504 A | 9/1991 | Albert et al. | |
| 5,101,828 A | 4/1992 | Welkowitz et al. | |
| 5,103,828 A | 4/1992 | Sramek | |
| 5,109,862 A | 5/1992 | Kelen et al. | |
| 5,170,794 A * | 12/1992 | Reiche | 600/484 |
| 5,178,151 A | 1/1993 | Sackner | |
| 5,178,154 A | 1/1993 | Ackmann et al. | |
| 5,309,917 A * | 5/1994 | Wang et al. | 600/508 |
| 5,423,326 A * | 6/1995 | Wang et al. | 600/526 |
| 5,443,073 A * | 8/1995 | Wang et al. | 600/526 |
| 5,503,157 A * | 4/1996 | Sramek | 600/506 |
| 5,694,939 A * | 12/1997 | Cowings | 600/484 |
| 5,879,308 A * | 3/1999 | Rasanen | 600/536 |
| 6,312,381 B1 * | 11/2001 | Knell et al. | 600/437 |
| 6,370,425 B1 * | 4/2002 | Oguma | 600/547 |
| 6,438,408 B1 * | 8/2002 | Mulligan et al. | 600/510 |
| 6,561,986 B2 * | 5/2003 | Baura et al. | 600/526 |
| 6,643,543 B2 * | 11/2003 | Takehara et al. | 600/547 |
| 6,829,503 B2 * | 12/2004 | Alt | 600/547 |
| 2001/0007055 A1 * | 7/2001 | Fukuda | 600/547 |
| 2001/0051774 A1 * | 12/2001 | Littrup et al. | 600/547 |
| 2002/0002389 A1 * | 1/2002 | Bradley et al. | 607/8 |
| 2002/0112898 A1 * | 8/2002 | Honda et al. | 177/245 |
| 2002/0193689 A1 * | 12/2002 | Bernstein et al. | 600/454 |
| 2003/0013982 A1 * | 1/2003 | Shimomura et al. | 600/547 |
| 2003/0055460 A1 * | 3/2003 | Owen et al. | 607/5 |
| 2003/0120164 A1 * | 6/2003 | Nielsen et al. | 600/513 |
| 2003/0163061 A1 * | 8/2003 | Miyoshi et al. | 600/547 |
| 2003/0220580 A1 * | 11/2003 | Alt | 600/547 |
| 2004/0006279 A1 * | 1/2004 | Arad | 600/506 |
| 2004/0015058 A1 * | 1/2004 | Besson et al. | 600/301 |
| 2004/0077969 A1 * | 4/2004 | Onda et al. | 600/547 |
| 2005/0070778 A1 * | 3/2005 | Lackey et al. | 600/366 |
| 2005/0101875 A1 * | 5/2005 | Semler et al. | 600/509 |

* cited by examiner

THORACIC IMPEDANCE MONITOR AND ELECTRODE ARRAY AND METHOD OF USE

CROSS-REFERENCE TO RELATED APPLICATIONS

This application claims benefit of U.S. Provisional Patent Application 60/556,394, "Electrode Array for Bioelectrical Device", filed Mar. 24, 2004.

BACKGROUND OF THE INVENTION

The present invention relates to the field of human impedance measurement devices.

It is known in the art to measure human impedance to monitor levels of intrathoracic fluids, such as blood. In particular, it is known to use an impedance monitor to measure human thoracic impedance, along with electrocardiogram (EKG) signals, as indicative of blood flow and heart performance characteristics, as described in U.S. Pat. No. 5,443,073(Wang et al.), the subject matter of which is incorporated by reference herein in its entirety. It is further known that certain medical conditions, such as congestive heart failure (CHF) or renal disease, correlate with the level and variation of the level of intrathoracic fluids.

Congestive heart failure results when the heart is unable to contract with sufficient vigor to meet the body's need for oxygen. Under such circumstances, to increase cardiac output, autoregulatory mechanisms allow the filling pressure in the ventricles to increase, thus elongating myocardial fibers at the start of systole and increasing the strength of contraction.

When the left and/or right filling pressures exceed approximately 15 mm Hg, blood components are forced out of the vasculature and into the interstitium, resulting in pulmonary edema (left heart failure) and/or peripheral edema and ascites (right heart failure). The end results are severe incapacitation and possibly death.

In a portion of the population with heart disease of many different etiologies—approximately 6,000,000 members of the U.S. population—the ability of the heart to meet the body's needs is marginal, resulting in chronic heart failure. For these patients, most of whom can be stabilized by medication and dietary restrictions and many of whom are quite elderly, minor variations in physical activity, emotional stress or non-compliance with diet or medication regimes can result in destabilization and episodes of acute heart failure requiring urgent hospitalization. Indeed, hospitalization for heart failure is the second most costly admitting diagnosis of the Medicare program.

There remains a need, however, for a practical and reliable method for monitoring the status of CHF patients outside of a hospital setting: with the goal of intervening before the onset of acute CHF. It would be most desirable to provide an easy-to-use and portable device for detecting increases in body water of patients with CHF before hospitalization is necessary and permitting adjustments in medication and/or diet in time to prevent an episode of acute heart failure. The present invention fulfills these needs and provides other related advantages.

The most reliable existing method to monitor CHF is by direct measurement of pulmonary artery and central venous pressures through catheters inserted into the bloodstream. This method, though highly accurate, is clearly impractical outside of a hospital setting. Other methods include observation of the arterial pressure pattern (invasively or noninvasively) during a Valsalva maneuver, measurement of flow though the mitral annulus and in the pulmonary veins using doppler echocardiography, observation of neck vein distension, measurement of ankle dimensions and careful tracking of body weight.

The first two methods, though reasonably accurate, require considerable equipment and trained personnel while the last three methods are quite unreliable for a variety of reasons.

Insertion of a cardiac catheter into the body may be hazardous. Its use can lead to death, which occurs in 1% of cases, and morbidity, which occurs in 33% of cases, as a result of infection and/or damage to the heart valves, cardiac arrhythmias, and pulmonary thromboembolism. Errors of technique, measurement, judgment and interpretation are common. It has been estimated that one-half million Swan-Ganz catheters used in the United States in 1986 resulted in the death of as many as 1000 or more patients. Furthermore, cardiac catheters cannot be kept in place for more than a few days owing to hazards from infection. They are also costly and labor intensive since catheterized patients require intensive care units which cost two to five times more than standard semi-private beds. In addition, health care workers face the risk of AIDS acquired virus and hepatitis virus as a result of exposure to blood of the infected patient during catheter introduction and subsequent maintenance. Moreover, cardiac catheters do not directly provide measurement of change in ventricular volume. While such measurements can be indirectly obtained in conjunction with injection of radiopaque dye and roentgenographic imaging, this technique is time-consuming and costly, and dangerous hypotension and bradycardia may be induced by the dye. Furthermore, the number of studies in a given patient is limited by the hazards of x-ray exposure and radiopaque dye injections.

Angiographic techniques provide the most widely accepted means for measuring ventricular volumes. They allow calculation of the extent and velocity of wall shortening and of regional abnormalities of wall motion. When they are combined with measurement of pressure, both ventricular compliance and afterload (i.e., the forces acting within the wall that oppose shortening) can be determined. When the results are expressed in units corrected for muscle length or circumferences of the ventricle, comparisons can be made between individuals with widely differing heart sizes.

Cineangiography provides a large number of sequential observations per unit of time, typically 30 to 60 frames per second. Although contrast material can be injected into the pulmonary artery and left atrium, the left ventricle is outlined more clearly when dye is directly injected into the ventricular cavity. Therefore, the latter approach is used in most patients, except in those with severe aortic regurgitation in whom the contrast material may be injected into the aorta, with the resultant reflux of contrast material outlining the left ventricular cavity.

Injection of a contrast agent does not produce hemodynamic changes (except for premature beats) until approximately the sixth beat after injection. The hyperosmolarity produced by the contrast agent increases the blood volume, which begins to raise preload and heart rate within 30 seconds of the injection, an effect that may persist for as long as two hours. Therefore, this technique cannot be utilized for repetitive measurements within a short time span. Further, contrast agents also depress contractility directly, though newer non-ionic agents have been found useful for minimizing these adverse effects.

In calculating ventricular volumes or dimensions from angiograms, it is essential to take into account and apply appropriate correction factors for magnification as well as distortion produced by nonparallel x-ray beams. In order to apply these correction factors, care must be taken to determine accurately the tube-to-patient and tube-to-film distances. Correction is best accomplished by filming a calibrated grid at the position of the ventricle. Thus, angiographic methods do not have wide clinical application owing to their complexity, safety considerations, invasiveness, and side effects of the contrast agents.

BRIEF SUMMARY OF THE INVENTION

According to one aspect of the invention, a thoracic impedance monitor is used for determining thoracic impedance of a user. The thoracic impedance monitor comprises an electrode array including a single linear electrode array lead and at least first, second, third, and fourth electrodes arranged axially along the single electrode array lead. The electrodes are connectable to the user at corresponding first, second, third, and fourth separate locations on a body of the user. A portable base unit is operatively connected to the electrode array lead. The base unit includes a power supply as well as circuitry operatively connected to one of the first and second electrodes and to one of the third and fourth electrodes for generating an electrical signal for delivery to the one of the first and second electrodes and to the one of the third and fourth electrodes. The base unit further includes circuitry operatively connected to the other of the first and second electrodes and the other of the third and fourth electrodes for detecting differential electrical potential and circuitry for calculating thoracic impedance of the user based upon the differential electrical potential. A display is provided for displaying the thoracic impedance of the user.

According to another aspect of the invention, a method of monitoring thoracic fluid level of a person comprises a step of providing a thoracic impedance monitor. The impedance monitor includes an electrode array including a single linear electrode array lead and first, second, third, and fourth electrodes arranged axially along the single electrode array lead and connectable to the user at respective first, second, third, and fourth separate locations on a body of the user. A portable base unit is operatively connected to the electrode array lead. The base unit includes a power supply and base unit circuitry including circuitry operatively connected to one of the first and second electrodes and to one of the third and fourth electrodes for generating an electrical signal for delivery to the one of the first and second electrodes and to the one of the third and fourth electrodes. The base unit circuitry further includes circuitry operatively connected to the other of the first and second electrodes and the other of the third and fourth electrodes for detecting differential electrical potential between the first and second electrodes and the third and fourth electrodes. Still further, the base unit circuitry includes circuitry for calculating thoracic impedance of the user based upon the differential electrical potentials. A start button operatively connects the power supply to the base unit circuitry. A display for displaying the thoracic impedance of the user is also provided in the base unit. The method further comprises a step of obtaining a measurement of the user's thoracic impedance by connecting the second electrode to the user's body at the junction of the clavicles, superior to the sternum, the third electrode to the user's body at the xyphiod-sternal junction, the first electrode to the user's body substantially along a centerline of the user's sternum at a first predetermined distance above the second electrode and the fourth electrode to the user's body substantially along the centerline of the user's sternum at a second predetermined distance below the third electrode. The method further includes the steps of: initiating operation of the thoracic impedance monitor by pressing the start button to apply a sinusoidal current to the first and fourth electrodes; detecting a differential electrical potential between the second and third electrodes; and recording the thoracic impedance reading of the user from the display.

According to yet another aspect of the invention, an electrode array for use with a physiological electronic monitor used to monitor electrical characteristics of a user's body comprises a single linear electrode array lead including at least first, second, third, and fourth electrodes arranged sequentially and axially along the linear electrode array lead.

BRIEF DESCRIPTION OF THE SEVERAL
VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

The present invention resides in an "early warning" monitoring system or "monitor" and a method for determining changes in the status of patients with chronic congestive heart failure (CHF), with the goal of intervening before the onset of acute congestive heart failure. The monitor can be used for other purposes such as determining relative hydration levels and/or fluid loss or retention in individuals such as athletes and dieters.

U.S. Provisional Patent Application 60/556,394, from which the present application claims priority, and U.S. Provisional Patent Application 60/549,739 titled "Base Impedance Fluid Monitor", filed on Mar. 3, 2004 and incorporated by reference in U.S. application Ser. No. 60/556,394, are both incorporated herein by reference in their entirety.

In accordance with the present invention, a process for monitoring patients comprises the steps of applying electrodes to points on the thorax symmetrically positioned with respect to the heart, passing a current at relatively high frequency and very low amperage between the electrodes, measuring the thoracic voltage (V) of the body, calculating an average thoracic (base) impedance value Zo based on the measured current (I) and the thoracic voltage (V) and displaying the average impedance value for comparison with baseline values previously established when the patient was in a known, stable condition, to determine if differences are within established tolerances. The process is preferably performed with a battery powered, portable base unit which performs all the necessary functions.

Figure 1:
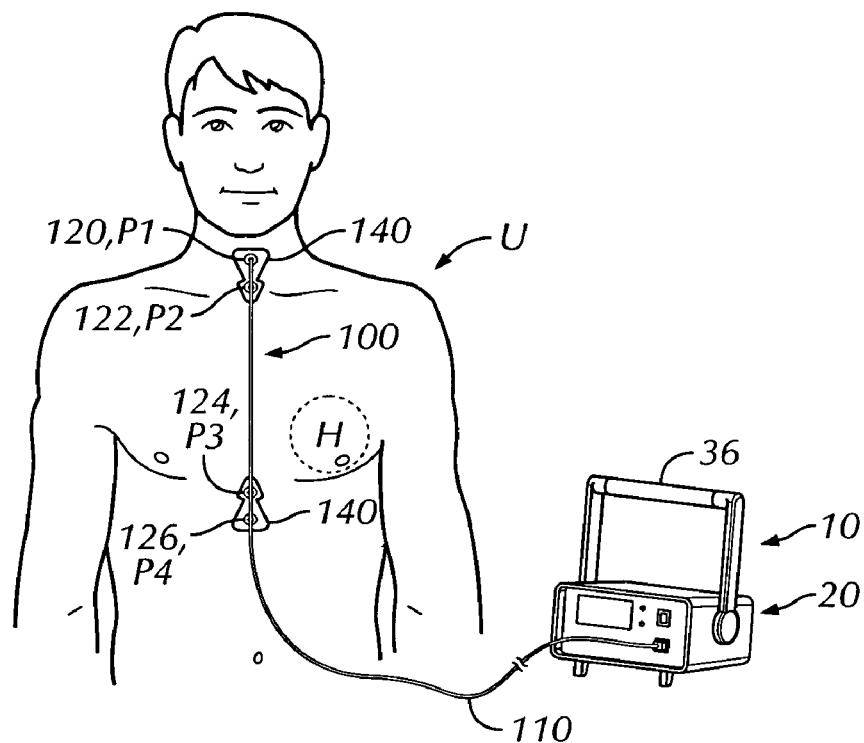
FIG. 1 depicts the impedance monitor of the present invention connected to a user.

FIG. 1 depicts a preferred embodiment of the monitoring system or "monitor" of the present invention which is indicated generally at 10 and which is shown installed on a user U. The system 10 measures thoracic impedance using a patient interface that includes a four electrode array assembly 100 which is coupled to a small, hand transportable base unit 20.

Figure 2:
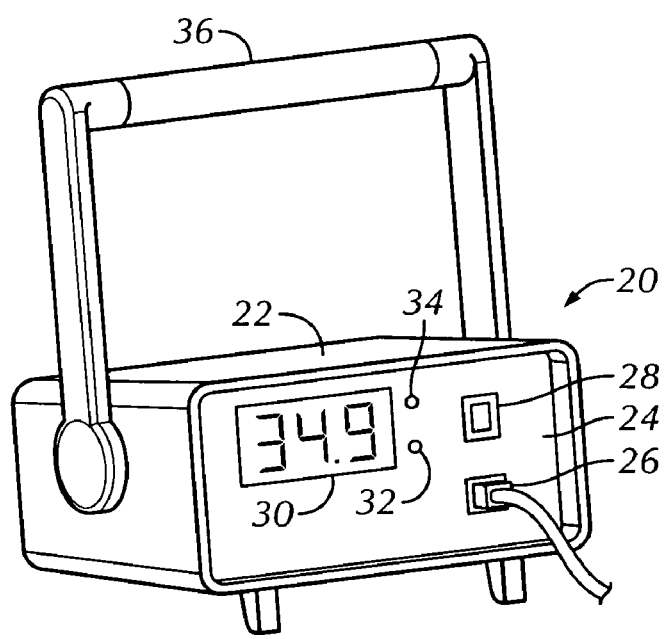
FIG. 2 is a front perspective view of the front face of a base unit of the monitor of FIG. 1.

FIG. 2 depicts a front panel 24 of the base unit 20. The base unit 20 is relatively lightweight (about one pound or one-half kilo) and is contained in a relatively small (i.e. hand transportable) housing 22. Preferably, the base unit 20 is provided with a handle 36 to facilitate transport. The base unit 20 contains several user interfaces in addition to a connector port 26 for receiving a connection end of the electrode array assembly 100. These interfaces preferably are a three digit display 30 (e.g. formed by three, seven segment LED's) which preferably digitally display impedance as xx.x ohms, a start switch 28 to start the system 10, a low battery alert light 32, and a cable disconnect alert light 34. Preferably the base unit 20 also contains a beeper 86 (see FIG. 4) or other sound generator for signaling purposes. Alternatively, additional alert lights (not illustrated) could be substituted for the beeper 86.

The base unit 20 is preferably configured to perform all necessary steps to measure, determine and display the patient's base impedance after the start switch 28 is actuated. However, the system 10 does not provide any patient diagnostic parameters. That is, it provides only a measurement of impedance over a predetermined fixed length of the patient's body. This value can be compared with other impedance values for the patient or against limit values and used as a relative measure of patient's "dryness" or "level of hydration". An analogy will be a blood pressure instrument which displays patient's systolic and diastolic blood pressure, but does not diagnose if a patient has hypertension or not. The information provided by system 10 will be evaluated along with various other parameters by health care or other professional to identify the use of the information for their specific purpose.

The base unit 20 will provide the following outputs. The three digit LED display 30 preferably will display impedance value as xx.x. During measurement, a rotating/flickering pattern can be displayed to indicate the measurement is in progress. To ensure that the user U records ONLY the impedance values, the system software preferably will not display any numerical values other than impedance value. This means that there should be no countdown timers and no error or diagnostic codes expressed as numerical values. The base unit 20 will also indicate an error condition (by the beeper or flashing lights) in the event it detects that it could not perform a valid impedance measurement or that the impedance value was outside of a predetermined measurement range (suggestedly 5 to 55 ohms). If the electrode array assembly is disconnected from the system cable disconnect alert light 34 will illuminate.

The base unit 20 will activate the low battery indication light 32 in the event it detects that the battery voltage is below a level that will allow for reliable impedance measurement. In the event of a low battery voltage condition, the base unit 20 may blink this LED 32, for example at a rate of once every 10 (+/−0.5) seconds for a period of 30 (+/−2) sec. If the battery voltage drops below 5.25 volts, but remains above 4.75 volts, the impedance results will be displayed along with blinking-battery condition LED 32 to indicate that the battery power is getting low but still acceptable. If the battery voltage drops below 4.75 volts, both LEDs 32, 34 can be made to blink to indicate that the battery voltage is low and accurate results could not be displayed. Preferably a micro-controller 80 in the base unit 20 will continue to operate below 4.75 volts, even though an accurate measurement cannot be made, to warn the user of the condition of the unit.

The base unit 20 can be configured to provide various beeper alerts to the user. Preferably the base unit 20 beeps to indicate that the measurement is completed and the displayed value should be recorded. The beeper 86 may further be activated to indicate other, different conditions or steps, for example, when the base unit 20 is initially activated, while the unit is initializing, while the power supply is stabilizing, while measurements are being taken and/or before the unit shuts itself off. The beeper 86 can also be activated in the event a successful measurement was not accomplished or an error condition was detected. Different beep patterns are suggestedly used for different conditions including different states of the base unit 20.

Referring to FIGS. 3A-3D, a first preferred embodiment of the electrode array assembly 100 of the present invention includes a single, linear electrode array lead 110 having a first end 112 and a second end 114. An electrical connector 116 is provided at the first end 112. Electrical connector 116 operatively connects to connector port 26. First through fourth electrodes 120, 122, 124, and 126 are arranged axially and spaced along the length of the lead 110. As discussed further below, preferably first and fourth electrodes 120, 126 are current sources, while preferably second and third electrodes 122, 124 measure electrical potential. Because the electrodes 120-126 are fixed along the lead 110, their spacing relative to one another is also fixed and predetermined, with the first and second electrodes 120, 122 being spaced a first pre-determined distance D1, and the third and fourth electrodes 124, 126 being spaced a second pre-determined distance D2. Preferably, with the first through fourth electrodes operatively connected to the user U, the first and second electrodes 120, 122 are spaced fully extended so as to be at the first pre-determined distance D1 on the user U and the third and fourth electrodes are spaced at the second pre-determined distance D2 on the user U. Preferably, the first and second pre-determined distances D1, D2 are equal and are optimal for accuracy of the impedance measurement. The first and second pre-determined distances D1, D2 are preferably about five cm (about two inches).

Preferably, identical first and second electrode pad assemblies 140 are releasably connectable to the electrodes 120-126. The preferred electrode pad assemblies include an overlapped arrow-shaped body member 142 into which are mounted a first electrode pad 146 and a second electrode pad 150. The body member 142 has a first side 142a, and the electrode pads 146, 150 are exposed on this first side 142a. On a second side 142b of the body member, male snap elements 152, rigidly connected to the electrode pads 146, 150, are exposed. The male snap elements 152 are adapted to releasably connect with complementary female snap elements 128 provided in the electrodes 120-126 on the lead 110. Any other conventional structure used for coupling electrode pads to such cardio leads may also be used.

Preferably, the body member 142 is pre-coated during manufacture with a contact adhesive on the first side 142a. A removable, adhesive protective film 144 is preferably provided. Preferably, the electrode pads 146, 150 are coated with an electrically conductive hydrogel which acts along with the contact adhesive and allows the electrode pads 146, 150 to releasably adhere to the user's skin. The electrodes 120-126 and electrode pads 146, 150 incorporated into the electrode array assembly 110 are preferably off-the-shelf commercially available components. The electrode pad assemblies 140 may be obtained from vendors such as Lead-Lok, Inc., Sandpoint, Id.

Figure 3A:
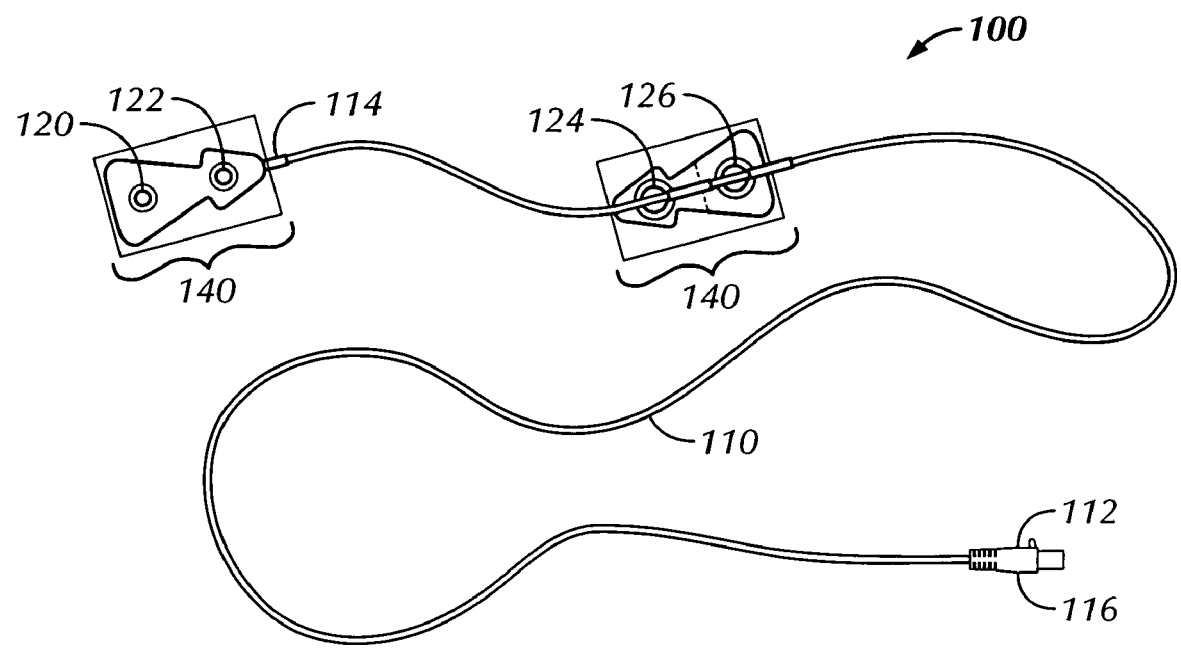
FIG. 3A is a perspective view of an electrode array assembly of the impedance monitor of FIG. 1, in accordance with a first preferred embodiment of the present invention.
Figure 3B:
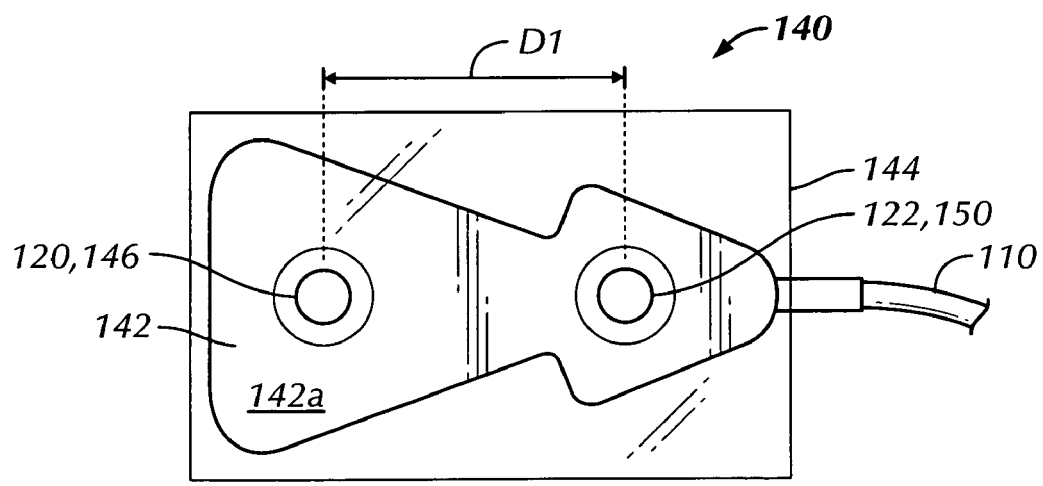
FIG. 3B is a plan view of a first side of an electrode pad assembly of the electrode array assembly of FIG. 3A.
Figure 3C:
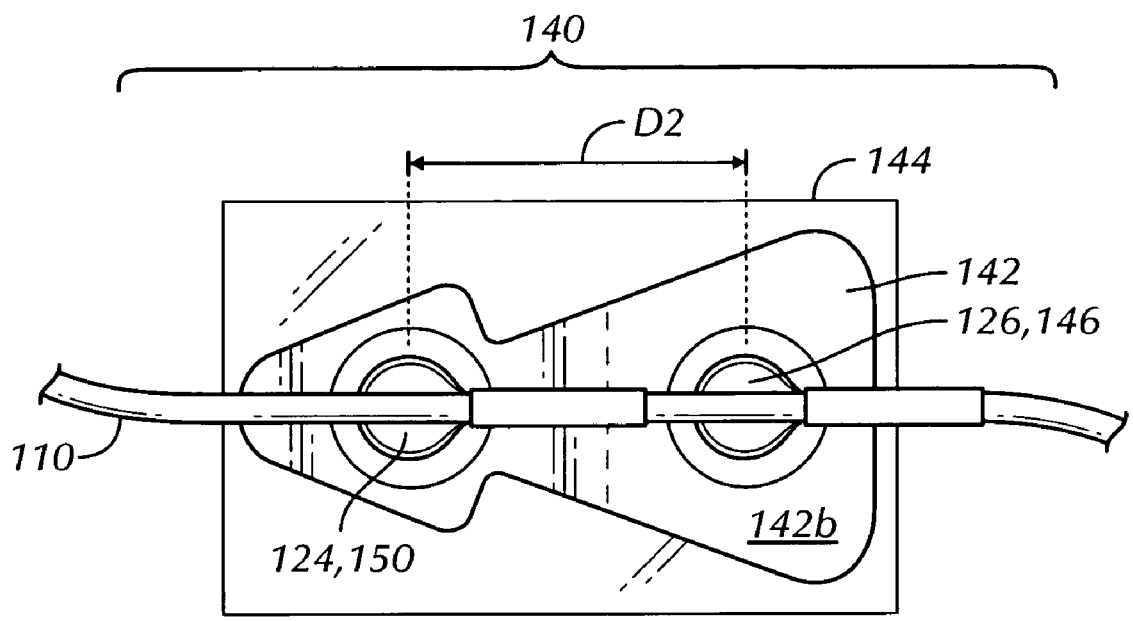
FIG. 3C is a plan view of a second side of an electrode pad assembly of the electrode array assembly of FIG. 3A.
Figure 3D:
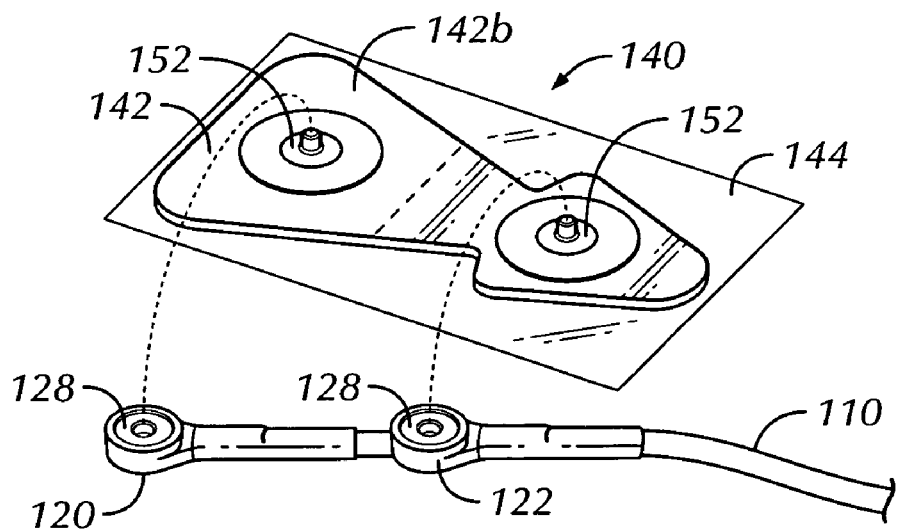
FIG. 3D is a plan view showing the electrode pad assembly of FIG. 3B separated from first and second electrodes of the electrode array assembly of FIG. 3A.
Figure 3E:
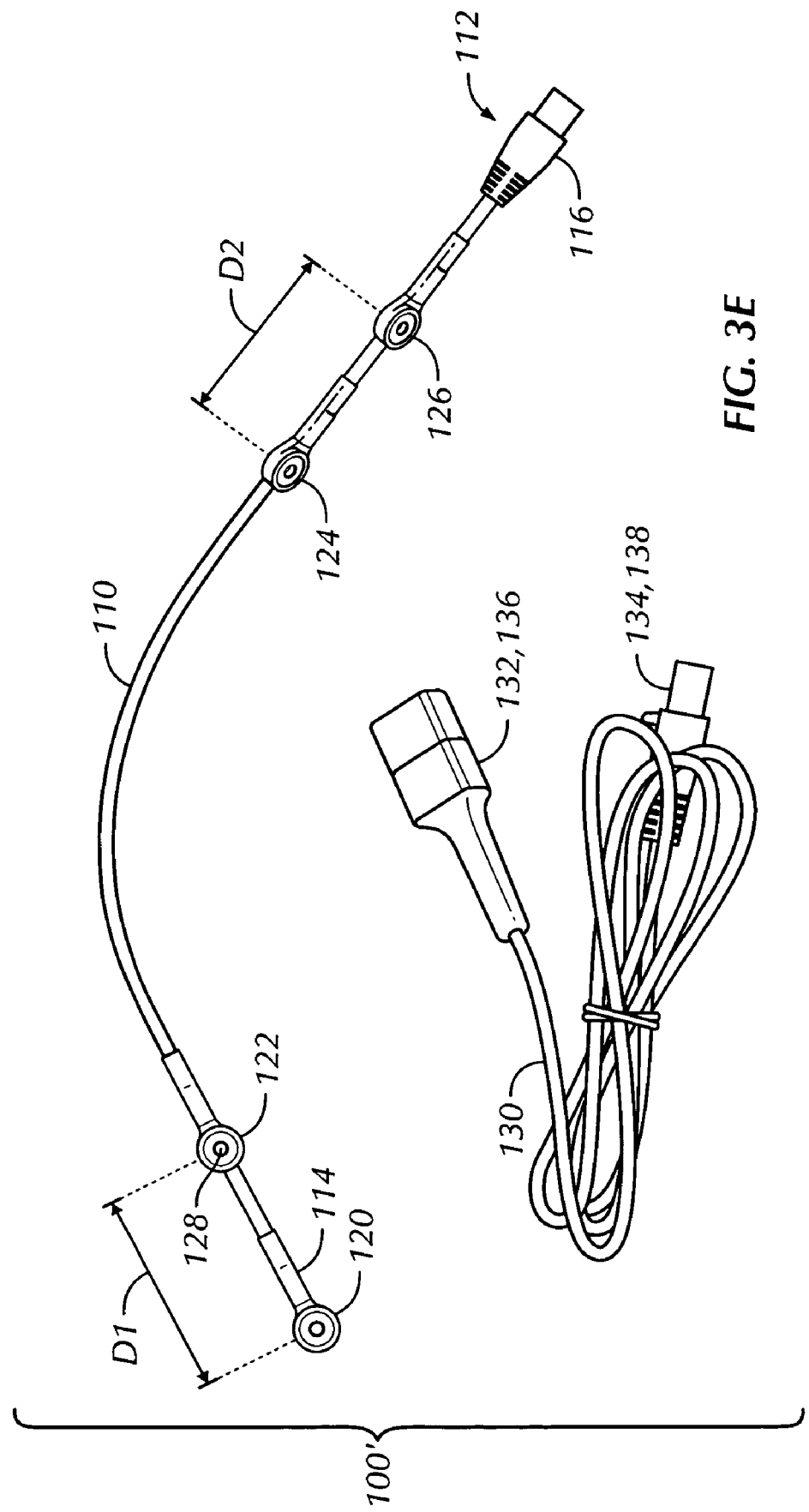
FIG. 3E is a perspective view of components of an electrode array assembly in accordance with a second preferred embodiment of the present invention.

Referring to FIG. 3E, a second preferred embodiment electrode array assembly 100' is generally similar to the first embodiment electrode array assembly 100, with the exception that a second embodiment electrode array lead 110' is substantially shorter, and a connection cord 130 is provided to connect the electrode array lead 110' to the base unit 20. The connection cord 130 has a first end 132, a second end 134, a first connector 136 at the first end 132 configured to mate with array lead connector 116, and a second connector 138 at the second end 134 configured to mate with base unit connector port 26. Note that electrode pad assemblies 140 are omitted from the illustration of FIG. 3E, but are used as part of the second embodiment electrode array assembly 100'.

With reference again to FIGS. 1 and 3A, to begin the process of applying the electrode array assembly 100, 100', the user first removes the adhesive protective film 144 from the first electrode pad assembly 140, exposing the first and second electrode pads 146, 150 connected to the first and second electrodes 120, 122. The user then applies the foam body member 142 to the user's body, connecting the second electrode pad 150 and the second electrode 122 to the user's body at the junction of the user's clavicles, superior to the sternum (location P2). The first electrode pad 146 and the first electrode 120 are then connected to the user's body substantially along a centerline of the user's sternum at the first pre-determined distance DI above the second electrode 122 (location P1). The user then proceeds to remove the adhesive protective film 144 from the second electrode pad assembly 140, exposing the first and second electrode pads 146, 150 connected to the third and fourth electrodes 124, 126. The user then applies the foam body member 142 to the user's body, connecting the second electrode pad 150 and the third electrode 124 to the user's body at the xyphiod-sternal junction (location P3), and the fourth electrode 126 to the user's body substantially along the centerline of the user's sternum at the second predetermined distance D2 below the third electrode 124 (location P4).

The array lead 110, 110' is flexible along its length. While the spacing between the first and second electrodes 120, 122 and between the third and fourth electrodes 124, 126 with the electrodes 120-126 operatively connected to a user is preferably the same for all users, given the flexibility of the array lead 110, 110', the spacing between the second electrode 122 and the third electrode 124 may be adjusted to accommodate users of various sizes. That is, for a user having a long sternum, with the electrodes 120-126 placed as indicated above, the electrode array lead 110, 110' will be more fully extended between the second and third electrodes 122, 124 than would be the case for a user having a shorter sternum and also having the electrodes 120-126 placed as indicated above. The electrode array assembly 100, 100' is fabricated from conventional cabling, electrical connector and medical electrode components.

Once a test is completed, the user removes the first and second electrode pad assemblies 140 from the user's body. Once used, the electrode pad assemblies 140 are removed from the electrode lead 110, 110' and discarded, and fresh electrode pad assemblies 140 are connected to the electrodes 120-126 in preparation for the next test.

It is noted that the inventive concept of the electrode array assembly 100, 100' is not limited in application to the thoracic impedance monitor. In particular, the electrode array assembly 100, 100' could be adapted for use with measurement devices within the general product class of impedance plethysmographs, sold under FDA regulation number 21 C.F.R. § 870.2770, regulatory class I1, product code 74 MNW.

Figure 4:
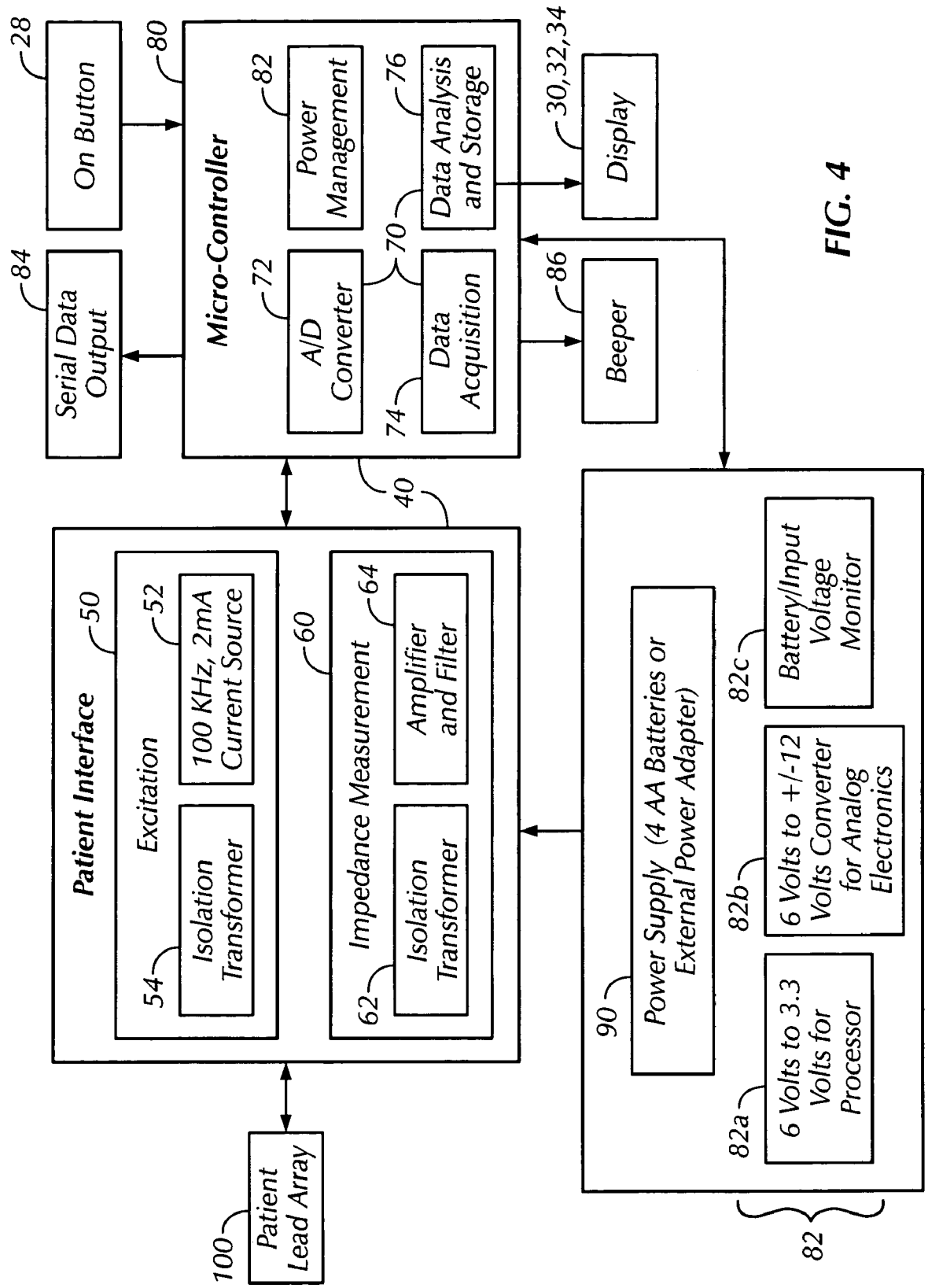
FIG. 4 is a block diagram of the major circuit components of the base unit.

With reference now to FIG. 4, a block diagram of the circuitry 40 of the base unit 20 indicates that the base unit circuitry 40 includes signal generating circuitry 50, voltage detection circuitry 60 and impedance calculation circuitry 70. The impedance calculation circuitry 70 includes an analog/digital converter 72, data acquisition circuitry 74, and data analysis and storage circuitry 76. Along with power management circuitry 82, the impedance calculation circuitry 70 is provided by a micro-controller 80.

The signal generating circuitry 50 generates the stable excitation current (I). A current source subcircuit 52 includes a constant current source (not depicted) and clock oscillator (not depicted) to supply a current of about 2 mA or less, preferably a 1.98±0.01 mA, at a 100±10 kHz (preferably, about 100 kHz) frequency preferably to the first and fourth electrodes 120, 126 through an isolation transformer 54, the connection cord 130 and electrode array lead 110. The current source subcircuit 52 is configured to output a current of less than 4 mA under all conditions including equipment component failure. The wave form of the current is suggestedly sinusoidal with less than ten percent total harmonic distortion. Voltage values across two of the four electrodes, preferably the second and third electrodes 122, 124, are passed through isolation transformer 62 to an amplifier and low pass filter subcircuit 64. The low pass filter subcircuit 64 functions to remove extraneous electrical interference from ambient sources, for example, home appliances operating on standard residential 60 Hz current. A preferred cut-off frequency of the low pass filter subcircuit 64 is about 50 Hz. The base unit 20 measures voltage developed across detection electrodes 122, 124 when the excitation current source is energized. The voltage level will be between about 18 millivolts and 104 millivolts (to provide an anticipated range of impedance measurement of about 10 ohms to 50 ohms, at the 2 mA current).

Micro-controller 80, which might be a PIC 16F873 device, controls generation of the excitation current and receives the filtered voltage analog signal from the amplifier and low pass filter 64 at the input of analog to digital converter 72. Suggestedly the injected current is not generated for a short period of time (e.g. fifteen to thirty seconds) after the start switch 28 is actuated to allow the user to settle into a quiescent state. Suggestedly the current is then injected for a predetermined period, e.g. thirty seconds, to perform the measurement. Voltage values sampled from the A/D converter 72 are received by the data acquisition circuitry 74 of the micro-controller 80 suggestedly at a rate of about five samples per second for all or most of the thirty second period. Data analysis and storage circuitry 76 of micro-controller 80 sums the counts generated by the A/D converter 72, divides sum by the total number of samples taken to provide an average voltage value which is converted into an impedance value. The algorithm used for generating impedance in tenths of ohms is: averaged A/D counts*Gain+Offset, where in the preferred circuit the Gain is 0.6112 and the Offset is 1.1074. Gain and Offset are based on the electronics design and operating range and are used for all base units 20. Each system 10 is calibrated to match the use of these numbers. The data analysis circuitry 76 also controls the various displays 30, 32, and 34. The power management circuitry 82 controls the generation and distribution of power in the base unit circuitry 40 to control operation of the system 10. Specific functions of the power management circuitry 82 include a first function 82a of providing power to the processor; a second function 82b of providing power to the A/D converter, and a third function 82c of monitoring the input voltage.

A power supply 90 may be provided by conventional dry-cell batteries (not shown) or by an external power adapter (not shown) connected to a conventional 120 V outlet.

The base unit 20 may be provided with a serial port 84 to work with logic level signals. The timing for the serial data can be similar to RS232 signal or other conventional data transfer format. The base unit 20 would preferably be provided with a serial port, for example one configured to operate at 9600 baud, with 8 bit data, 1 Start bit, 1 Stop bit and no parity bit format. An external level translator may be necessary to interface the base unit to a PC or a PALM device. Upon receipt of a specific command, the base 20 unit would be configured to transmit the information related to all or a subset (e.g. the last ten) of the readings of the impedance measurement. This information may also include the date and time of measurement, impedance value, and/or the serial number of the unit.

Figure 5:
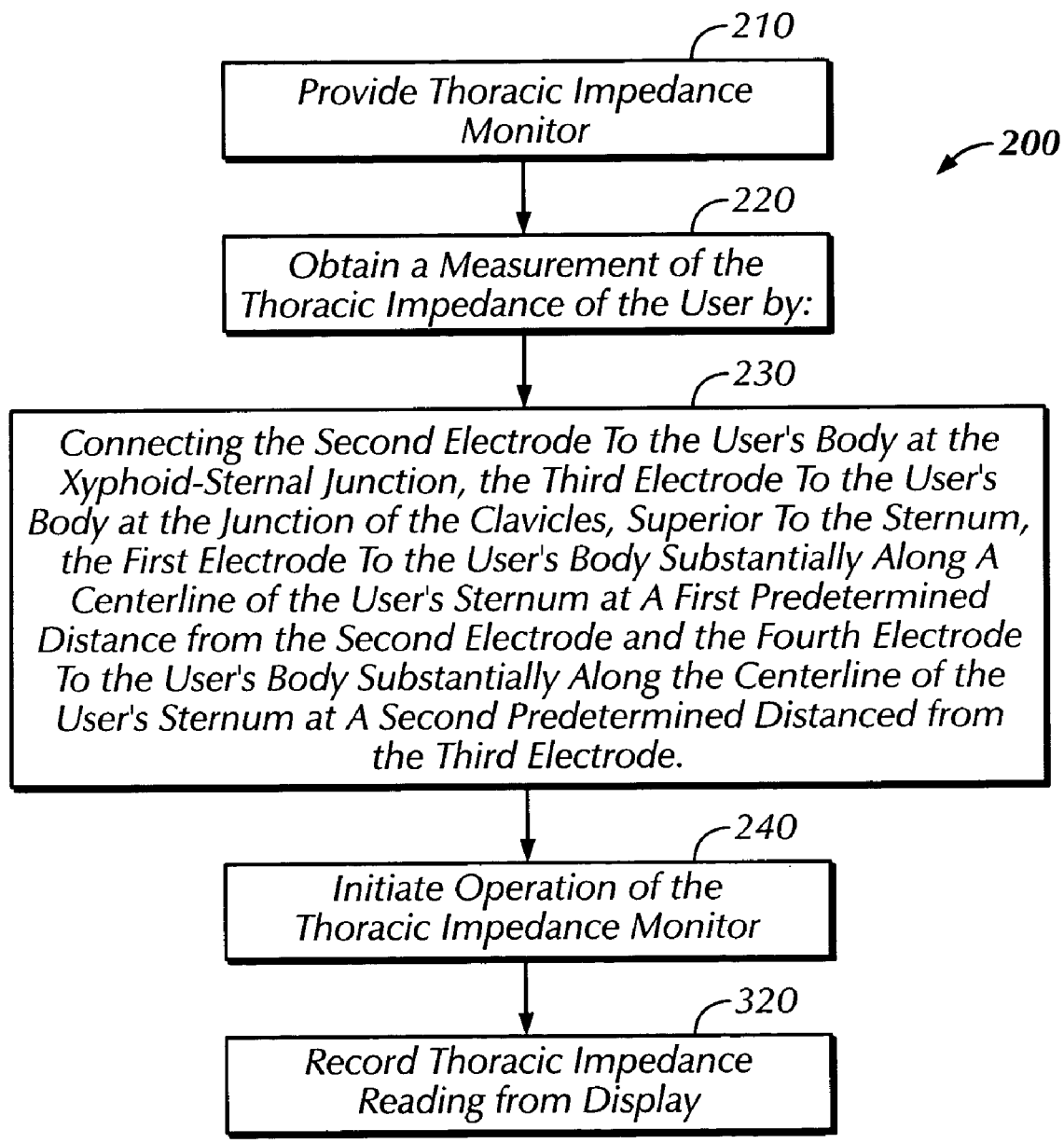
FIG. 5 is a diagram of steps of a method of monitoring thoracic fluid level of a person in accordance with the present invention.
Figure 6A:
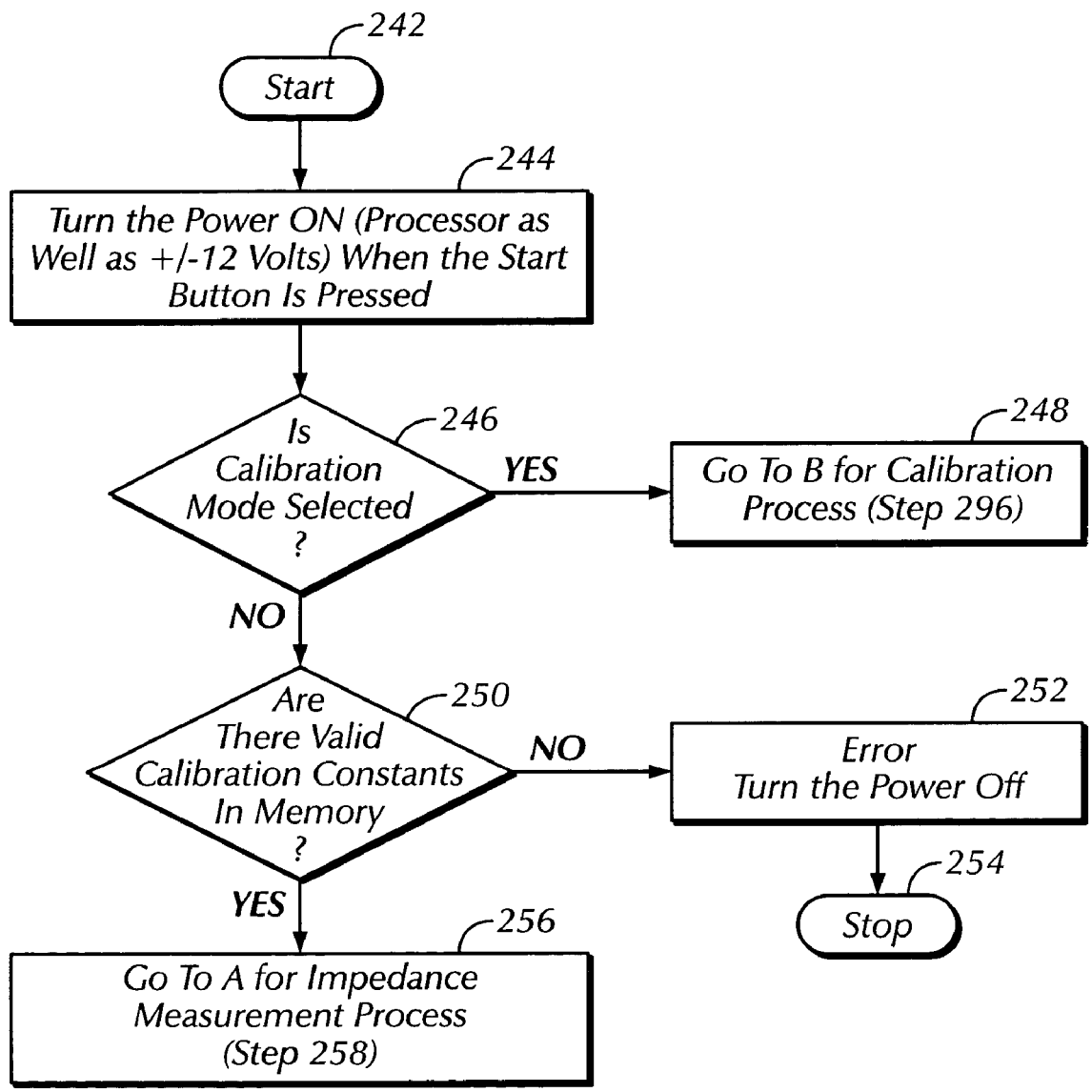
FIGS. 6A-6D are flow diagrams describing in detail operation of the base unit.
Figure 6B:
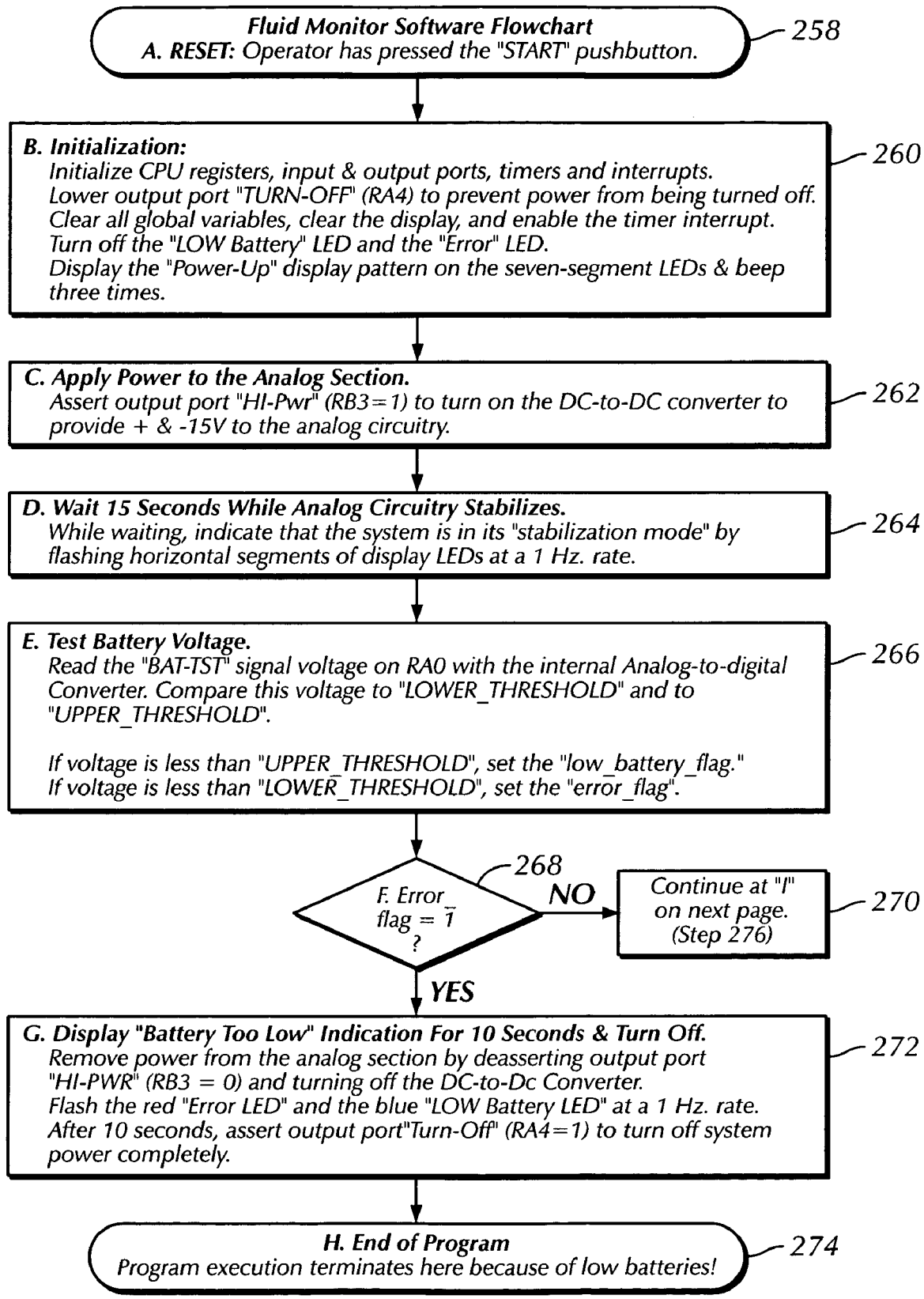
Figure 6C:
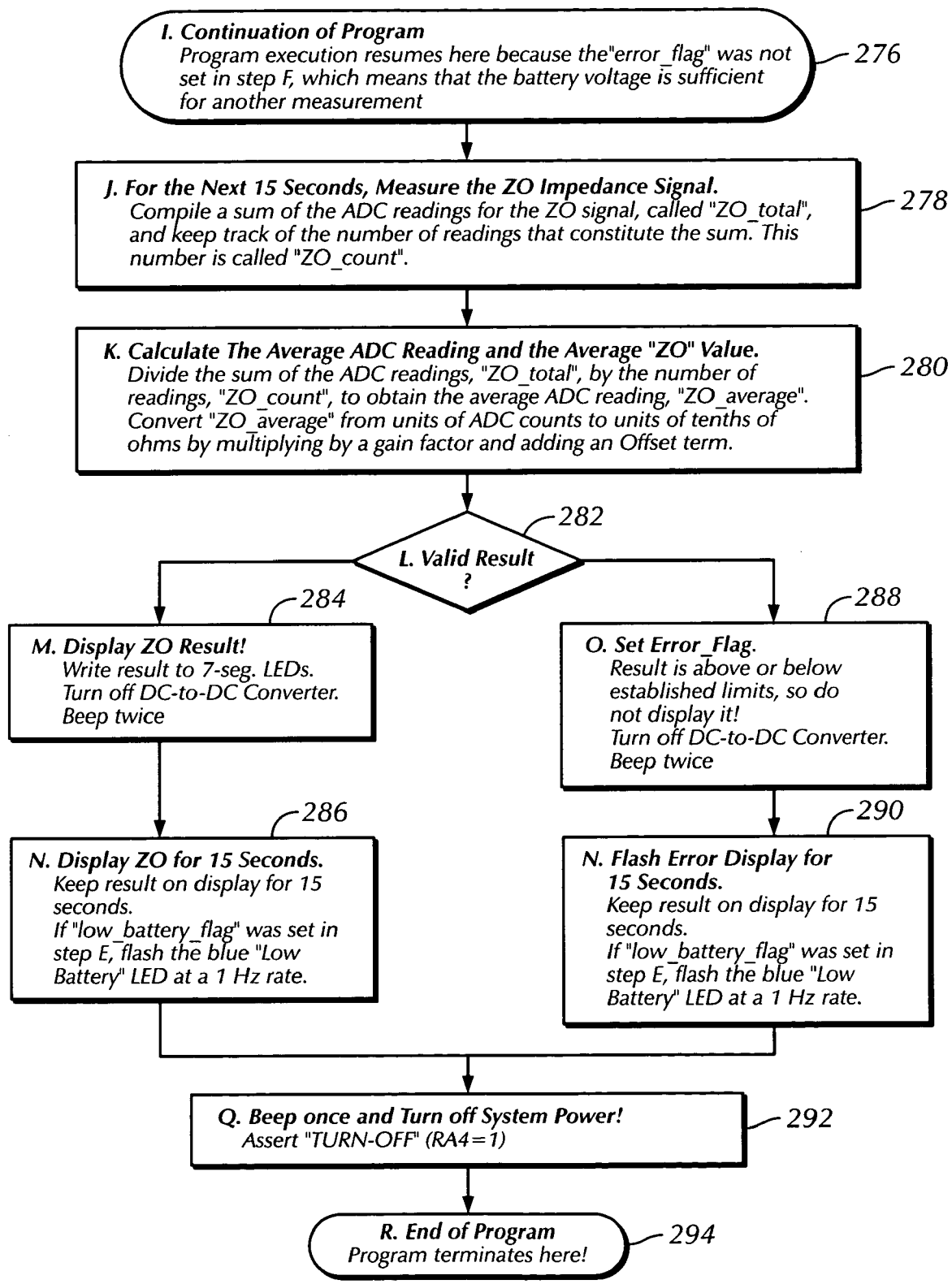
Figure 6D:
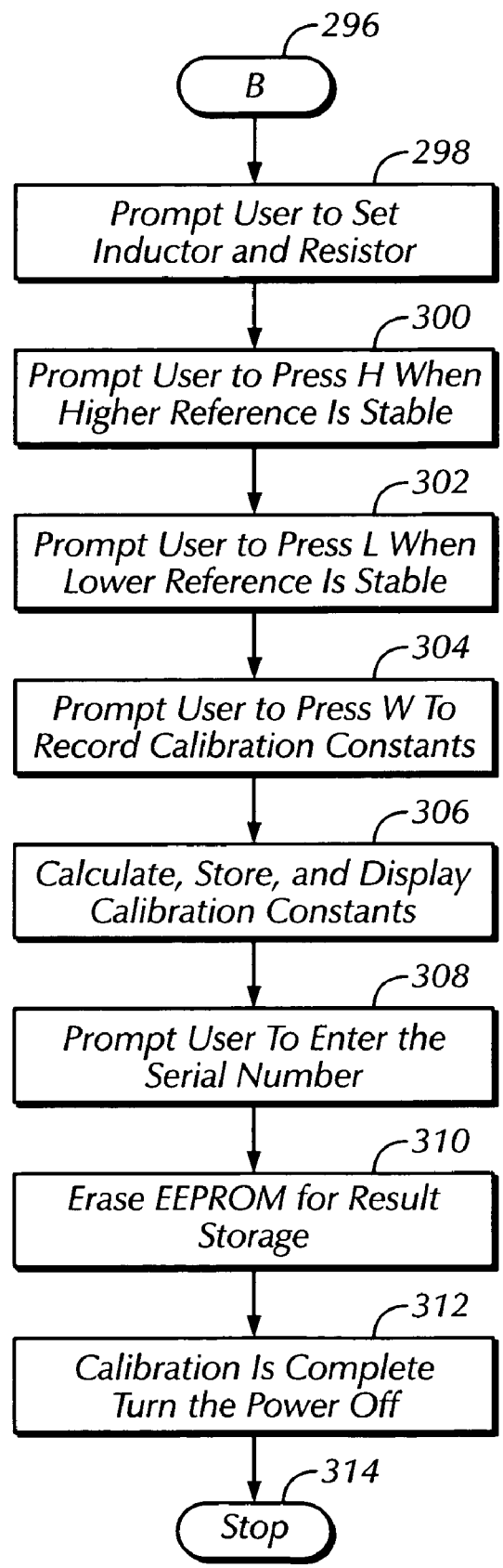

With reference to FIG. 5, a method of monitoring thoracic fluid level of a person includes a first step 210 of providing the thoracic impedance monitor 10, as described herein. In a second step 220, the user obtains a measurement of their thoracic impedance. To accomplish this second step 220, in a third step 230, the user connects the first through fourth electrodes 120-126, via electrode pads 146, 150, to the users' body, as described above.

With the electrodes 120-126 in place, in a fourth step 240, the user may initiate operation of the impedance monitor 10 by actuating the start switch 28. The user should remain "relatively" still for the length of the measurement period. The system 10 will inject the relatively high frequency (e.g. about 100 KHz) very low amperage (about 2 or less mA) current into the user and take voltage readings from the second and third electrodes 122, 124 for a period of time (e.g. about thirty seconds), calculate the average thoracic (base) impedance and then display the average value, preferably for a predetermined period (e.g. fifteen seconds to two minutes). In particular, activation of the start switch 28 initiates a series of steps 242-314. For brevity, the reader is referred to FIGS. 6A-6D, which describe in detail the series of steps 242-314. In short, assuming proper functioning of the impedance monitor 10, activation of the start switch 28 culminates in display of the user's thoracic impedance (measured in ohms) on the base unit display 30. Once the reading is obtained, in a fifth step 320, it is desirable that the user log the reading into a record of impedance measurements taken over time.

Preferably, the user need use the system 10 only once a day but may take it more than once a day if need or desired. The total time required for a test is brief, approximately five minutes. Preferably, to improve the ability to compare measurements, the measurements are taken at the same time of day (thoracic impedance measurements typically vary over the course of a day, as eating, drinking, and other activities affect thoracic fluid levels). More preferably, the test is performed daily before the user eats his or her first meal of the day. The test may be taken more often, for example, to monitor the effects of medication (e.g. diuretics) or exercise.

A thoracic impedance monitor 10 providing a high degree of ease of use is thus disclosed. The impedance monitor 10 of the present invention allows a user to quickly and easily apply the electrode array to the user's body in a manner that results in accurate and repeatable test measurements. The electrode array is thus especially well adapted for home use.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A method of using an electrode array and operably coupled impedance measuring device that comprises an electrode array for use with a physiological electronic monitor used to monitor electrical characteristics of a user's body, comprising a single linear electrode array lead including at least first, second, third, and fourth electrodes arranged sequentially and axially along the linear electrode array lead; a first electrode pad assembly including a body member mounting first and second conductive electrode pads, the first and second conductive electrode pads being spaced apart from one another the first pre-determined distance on the body member and being exposed on one side of the body member for contact with the user's body, each electrode pad being coupled with a separate one of the first and second electrodes; and a display configured to display user impedance determined by the device using the electrode array; wherein the first and second electrodes are spaced apart a first pre-determined distance by a first portion of the electrode lead and the third and fourth electrodes are spaced apart a second pre-determined distance by a second portion of the electrode lead equal to the first pre-determined distance; wherein the electrode lead is sufficiently flexible between the second and third electrodes to vary the distance between the second and third electrodes on the user's body; and wherein the second and third electrodes are spaced apart from one another by a third portion of the electrode lead a distance sufficient to at least mount one of the second and third electrodes to any adult user's thorax at the junction of adult user's clavicles and the other of the second and third electrodes to the user's thorax just beyond the user's xiphoid-sternal junction away from the clavicles; the method comprising the steps of:

electrically connecting the second electrode to the user's thorax at the junction of the clavicles, superior to the sternum, the third electrode to the user's thorax proximal the xiphoid-sternal junction, the first electrode to the user's body substantially along a centerline of the user's sternum at the first pre-determined distance above the second electrode and the fourth electrode to the user's thorax substantially along the centerline of the user's sternum at the second predetermined distance below the third electrode;

applying a sinusoidal current from the impedance measuring device to the first and fourth electrodes and detecting a differential electrical potential between the second and third electrodes with the impedance measuring device;

determining thoracic impedance of the user from the detected differential electrical potential;

displaying a numerical value of determined thoracic impedance on the display of the impedance measuring device;

wherein the detecting step comprises the steps of differentially amplifying and low pass filtering voltages from the second and third electrodes; and wherein the calculating step comprises the steps of sampling the differentially amplified and low pass filtered thoracic voltage from the second and third electrodes at predetermined intervals for a number of times, adding the sampled thoracic voltages to generate a sum, dividing the sum by the number of times to provide an averaged thoracic voltage value; scaling the averaged thoracic voltage value and combining the scaled averaged thoracic voltage value with a predetermined offset value to generate a numerical value of the differential thoracic impedance.

2. The method of claim 1 wherein the method further comprises the step of displaying the numerical value of the differential thoracic impedance on the display, the numerical value of the differential thoracic impedance being the only numerical value displayed on the display.

3. The method of claim 2 comprising the step of selecting as the user, a person suffering from chronic heart failure, wherein at least the steps of initiating operation, detecting, calculating and displaying the numerical value of the differential thoracic impedance of the person are repeated on at least a daily basis and further comprising the step of monitoring progress of the chronic heart failure of the user from the differential thoracic impedance values of the user.

4. The method of claim 1 wherein the user's thoracic impedance is measured on at least a daily basis to monitor the thoracic fluid level of the user.

5. The method of claim 4, wherein the daily measurements are taken at substantially the same time during the day.

6. The method of claim 5, wherein the daily measurements are taken before the user eats a first meal of the day.

7. The method of claim 1 wherein the user's thoracic fluid level is monitored; and each of the first, second, third and fourth electrodes is electrically coupled with an electrode pad and wherein the connecting step comprises the step of adhering the electrode array to the thorax of the user so as to operatively couple each of the first, second, third and fourth electrode pads to the user's outer skin in line with the user's sternum.

8. The method of monitoring thoracic fluid level of claim 7 wherein the first through the fourth electrodes are the only electrodes connected between the user and the base unit during the initiating operation step.

9. The method of monitoring thoracic fluid level of claim 8 further comprising between the initiating operation and the recording steps, the steps of determining a numerical value of thoracic impedance of the user and displaying the numerical value on the display.

10. A thoracic impedance monitor for determining thoracic impedance of a user, comprising:

an electrode array including a single linear electrode array lead and at least first, second, third, and fourth electrodes arranged axially along the single electrode array lead and connectable to the user at corresponding first, second, third, and fourth separate locations on a body of the user; and a portable base unit operatively connected to the electrode array lead, including:

a power supply;

circuitry operatively connected to one of the first and second electrodes and to one of the third and fourth electrodes for generating an electrical signal for delivery to the one of the first and second electrodes and to the one of the third and fourth electrodes;

circuitry operatively connected to the other of the first and second electrodes and the other of the third and fourth electrodes for detecting differential electrical potential;

circuitry for calculating a numerical value of thoracic impedance of the user based upon the differential electrical potential; and a display for displaying the numerical value of thoracic impedance of the user;

wherein the second electrode is operatively placed on the user's body at the junction of the user's clavicles, superior to the sternum and the third electrode is placed on the user's body at the xiphoid-sternal junction;

wherein the first electrode is placed higher on the user's body substantially along a centerline of the user's sternum at a first predetermined distance from the second electrode and the fourth electrode is placed lower on the user's body substantially along the centerline of the user's sternum at a second pre-determined distance from the third electrode;

wherein the first and second electrodes are spaced on the electrode array lead at the first pre-determined distance and the third and fourth electrodes are spaced on the electrode array lead at the second pre-determined distance, such that with the electrode array lead fully extended, the first and second electrodes are spaced apart the first pre-determined distance and the third and fourth electrodes are spaced apart the second pre-determined distance;

wherein the first and second pre-determined distances are each about five cm (about two inches); and wherein the circuitry for calculating thoracic impedance is configured to sample thoracic voltage through the second and third electrodes at predetermined intervals for a number of times, add the sampled thoracic voltages to generate a sum, divide the sum by the number of times to provide an averaged thoracic voltage value; scale the averaged thoracic voltage value and combine the scaled averaged thoracic voltage value with a predetermined offset value to generate a numerical value of the differential thoracic impedance displayed on the display.

11. The thoracic impedance monitor of claim 10 wherein the numerical value of the differential thoracic impedance is the only numerical value the circuitry of the portable base unit is configured to display on the display.

12. The thoracic impedance monitor of claim 11 wherein the circuitry for detecting differential electrical potential consists essentially of a low pass filter, a differential amplifier and an analog to digital converter operably connected between the second and third electrodes and the circuitry for calculating thoracic impedance.

13. The thoracic impedance monitor of claim 10 wherein the first through fourth electrodes are the only electrodes provided to connect between the user's body and the base unit to measure thoracic impedance.

14. The thoracic impedance monitor of claim 10, wherein the electrical signal is delivered to the first and fourth electrodes and the differential electrical potential is measured between the second and third electrodes.

15. The thoracic impedance monitor of claim 10, wherein the circuitry generating an electrical signal generates a current of about 2 mA and the circuitry detecting differential electrical potential detects a voltage in the range of about 20 mV to about 100 mV, corresponding to a thoracic impedance of the user in the range of about 10 to about 50 ohms.

16. The thoracic impedance monitor of claim 10, wherein the electrical signal is a pure sinusoidal wave generated by electrical components including a constant current source and a clock oscillator.

17. The thoracic impedance monitor of claim 16, wherein the electrical signal has a frequency in the range of about 90 kHz to about 110 kHz and current in the range of about 1.97 mA to about 1.99 mA.

18. The thoracic impedance monitor of claim 17, wherein the electrical signal has a frequency of about 100 kHz and a current of about 1.98 mA.

19. The thoracic impedance monitor of claim 10, wherein the base unit further including a handle to facilitate transport of the base unit.

20. The thoracic impedance monitor of claim 10, wherein the power supply is provided by batteries.

21. The thoracic impedance monitor of claim 10, the base unit further including a serial data port.

22. The thoracic impedance monitor of claim 10 wherein the electrode array includes at least first, second, third, and fourth electrodes arranged sequentially and axially along the linear electrode array lead;
wherein the first and second electrodes are spaced apart a first pre-determined distance by a first portion of the electrode lead and the third and fourth electrodes are spaced apart a second pre-determined distance by a second portion of the electrode lead equal to the first pre-determined distance; and
wherein the electrode lead is sufficiently flexible between the second and third electrodes to vary the distance between the second and third electrodes on the user's body.

23. The thoracic impedance monitor of claim 22 wherein the first, second, third and fourth electrodes are arranged consecutively along the array and wherein the second and third electrodes of the array are spaced apart a distance along the array greater than the equal pre-determined first and second distances and sufficient to position one of the second and third electrodes on the thorax of any adult user at a junction of the adult user's clavicles and the other of the second and third electrodes on the thorax of the adult user just beyond the adult user's xiphoid-sternal junction away from the clavicles and further comprising adhesive located on the electrode array so as to adhere each of the first, second, third and fourth electrodes to skin of the user's thorax.

24. The thoracic impedance monitor of claim 22 further comprising a first electrode pad assembly of the electrode array including a body member mounting first and second conductive electrode pads, the first and second conductive electrode pads being spaced apart from one another the first pre-determined distance on the body member and being exposed on one side of the body member for contact with the user's body, each electrode pad being coupled with a separate one of the first and second electrodes.

25. The thoracic impedance monitor of claim 24 further comprising a second electrode pad assembly of the electrode array identical to the first electrode pad assembly and releasably coupled with the third and fourth electrodes.

26. The thoracic impedance monitor of claim 24 wherein the second and third electrodes of the electrode array are spaced apart from one another by a third portion of the electrode lead a distance sufficient to at least mount one of the second and third electrodes to any adult user's thorax at the junction of adult user's clavicles and the other of the second and third electrodes to the user's thorax just beyond the user's xiphoid-sternal junction away from the clavicles.

27. The thoracic impedance monitor of claim 10 wherein the electrode array further comprises: electrode pads electrically coupled with each of the first, second, third and fourth electrodes; and adhesive located to operatively couple each of the first, second, third and fourth electrode pads to the user's outer skin in line with the user's sternum.

* * * * *